Figure 1:
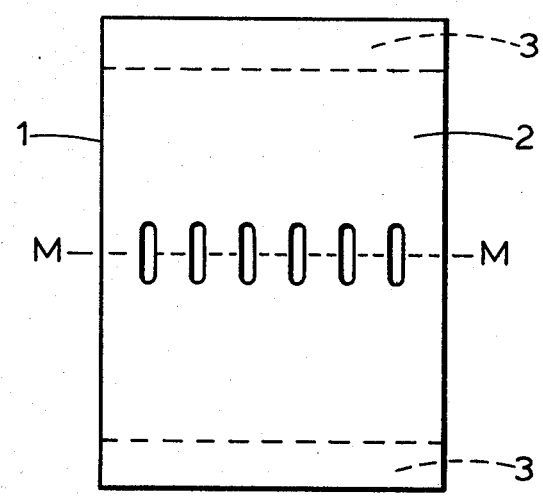
Figure 2:
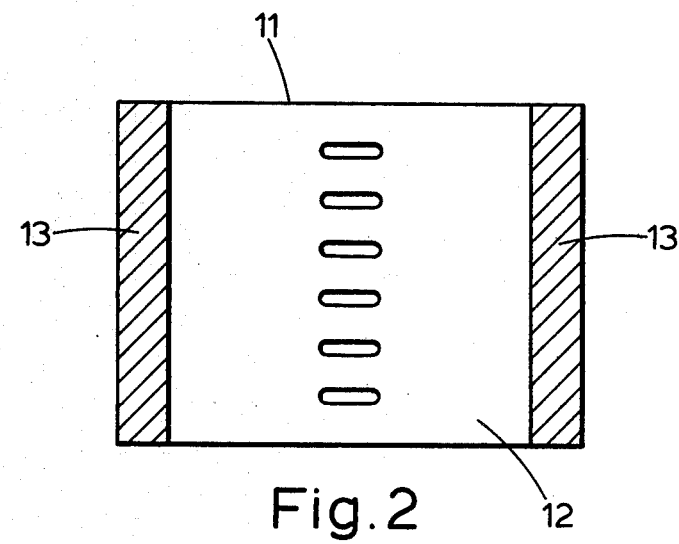

United States Patent [19]

Sanderson

[11] 4,370,981
[45] Feb. 1, 1983

[54] PROTECTIVE DEVICES AND METHODS

[75] Inventor: Brian A. Sanderson, Broom, Nr. Biggleswade, England

[73] Assignee: Smith & Nephew Associated Companies, Ltd., London, England

[21] Appl. No.: 189,621

[22] Filed: Sep. 22, 1980

[30] Foreign Application Priority Data

Sep. 27, 1979 [GB] United Kingdom ............... 7933560
Feb. 15, 1980 [GB] United Kingdom ............... 8005292
Mar. 1, 1980 [GB] United Kingdom ............... 8007047

[51] Int. Cl.³ ............................................. A61F 13/02
[52] U.S. Cl. ................................... 128/334 R; 128/335
[58] Field of Search .................. 428/500; 128/334 R, 128/335, 156

[56] References Cited

U.S. PATENT DOCUMENTS

| | | | |
|---|---|---|---|
| 2,711,739 | 6/1955 | Yishbein | 128/335 |
| 2,722,220 | 11/1955 | Nestrand | 128/334 R |
| 2,807,262 | 9/1957 | Lew | 128/156 |
| 3,086,531 | 4/1963 | Schiitz | 128/335 |
| 3,645,835 | 2/1972 | Hodgson | 428/500 |

FOREIGN PATENT DOCUMENTS

| | | | |
|---|---|---|---|
| 6927955 | 7/1969 | Fed. Rep. of Germany . | |
| 2000270 | 7/1970 | Fed. Rep. of Germany . | |
| 2045941 | 3/1972 | Fed. Rep. of Germany . | |
| 2733549 | 2/1978 | Fed. Rep. of Germany . | |
| 928389 | 5/1946 | France . | |
| 994197 | 11/1951 | France . | |
| 831401 | 3/1960 | United Kingdom | 128/335 |
| 1299367 | 12/1972 | United Kingdom | 128/335 |

Primary Examiner—V. Millin
Assistant Examiner—Nancy A. B. Swisher
Attorney, Agent, or Firm—Jacobs & Jacobs

[57] ABSTRACT

The present invention provides a flexible adhesive skin closure of the type which has a central portion provided with apertures sufficient for the manipulation of wound edges, said skin closure being made of a material which is flexible, elastic, air permeable and being impervious to bacteria and liquid which comprises a film coated on one surface with an adhesive.

5 Claims, 2 Drawing Figures

PROTECTIVE DEVICES AND METHODS

This invention relates to a skin closure useful in the medical art and particularly useful in the care and treatment of incisions and lacerations.

It is commonplace in the treatment of surgical incisions or accidental lacerations to unite the edges of the tissue by suturing, with a skilled operator using a special needle and thread and usually a specialised knotting technique. This is cheap and effective but is somewhat painful to a conscious patient. Moreover, sutures are foreign bodies which can induce painful inflammation and can provide a tract for bacterial migration thereby reducing the rate at which the wound heals. An alternative proposal to unite the edges of an incision or laceration is by the use of flexible adhesive closures applied across the incision or lacerations after this has been manipulated into the desired abutment of its edges. These closures have some advantages over the prior method. For example they need much less skill to apply and remove, are more comfortable from the patients viewpoint and are non-evasive so that they do not initiate inflammation or foreign body reaction. Additionally because there is no skin penetration they tend to give a better build-up of strength within the scar tissue than do sutures.

U.S. Pat. No. 3,086,531 described a considerable step forward in the art in which a flexible adhesive closure was provided with a central portion to lie over the incision or laceration which is free from adhesive and is provided with closely spaced parallel elongate openings extending longitudinally with regard to the closure. With such closure the wound can be observed through the elongate openings during the healing process to check on any ulceration or scar-formation while the edges are held together. To ensure non-adhesion in the central portion the Specification envisaged a wound-compatible covery layer of synthetic material or of metal foil, in each case equivalently and simultaneously perforated with the elongate openings and inextensible in nature. Such a closure is somewhat complex to manufacture, especially when involving a metal foil. It is typically embodied as a narrow strip and these are awkward to handle and time-consuming when several are required to dress a lengthy incision or laceration. Also the margins lying immediately to either side of the incision line are not gripped so that they can move laterally while the tissues are still disunited or only weakly united. This is due in part to the "lands" between the orifices, as described in U.S. Pat. No. 3,086,531 being very narrow. Attempts to remedy such defects by applying adhesive to the closure in the central portion as well as the ends has not proved particularly successful in view of the poor adhesion experienced which may be due to wound exudate.

U.S. Pat. No. 3,645,835 discloses inter alia the great advantages involved in making adhesive medical and surgical dressings of adhesive materials of high moisture vapour permeability. Particularly suitable applications of the materials disclosed in that patent included surgical drapes, suture strips and the like. One of the many considerable advantages that followed from the use of the materials of U.S. Pat. No. 3,645,835 was that a large area could be kept sterile owing to the continuous nature of the preferred materials. Since the skilled art worker is well aware of the general desirability of keeping as much as possible of the area around the wound sterile to would not be considered sensible to deliberately rupture the adhesive dressing in the area of the wound. However it has now surprisingly been found that inclusion of orifices in an adhesive dressing of the type disclosed in U.S. Pat. No. 3,645,835 allows the preparation of a skin closure having very desirable properties. In particular it has been found that excellent results may be obtained by using a flexible, elastic, air permeable, moisture vapour permeable sheet which is impervious to bacteria and liquid and which comprises a polyurethane film coated on one surface with an adhesive. A material of this type may be presently obtained from T. J. Smith and Nephew Limited, Welwyn Garden City and Hull, England as "Op-Site" (Registered Trade Mark).

The present invention provides a flexible adhesive skin closure of the type which has a central portion provided with apertures sufficient for the manipulation of wound edges, said skin closure being made of a material which is flexible, elastic, air permeable and being impervious to bacteria and liquid and which comprises a film coated on one surface with an adhesive. Alternatively this may be expressed as a flexible adhesive skin closure of the type which has a central portion provided with apertures sufficient for the manipulation of wound edges characterised in that said skin closure comprises a film coated on one surface with an adhesive and is flexible, elastic, air permeable and impervious to bacteria and liquid.

Naturally the film will be biocompatible. Naturally the adhesive will also be biocompatible. Such characteristics are obviously necessary for use in a skin closure.

Most suitably the skin closure of this invention is made of moisture vapour permeable materials so that the closure is moisture vapour permeable which produces very desirable properties such as being suitable for long duration use.

Since the skin closure of this invention is flexible and elastic it will conform to the body surface in the area of the wound and if applied under tension will draw the opposing edges of the wound towards each other.

When used herein the term "flexible and elastic" is most suitably applied to adhesive coated films having a promply recoverable stretch of at least 20% when a tension of up to 400 g per 2.5 cm width is applied thereto, favourably at least 8% when a tension of up to 300 g per 2.5 cm width is applied thereto and preferably at least 20% when a tension of 300–400 g per 2.5 cm width is applied thereto. (Such values may be determined at skin temperature, for example 30° C., in conventional manner).

When used herein the term "moisture vapour permeable" suitably means a permeability of at least 300 g/m$^2$, more suitably at least 500 g/m$^2$ and preferably at least 700 g/m$^2$/day/40° C. /100–20% relative humidity difference. (The method of U.S. Pat. No. 3,645,835 may be used to measure permeability. Naturally the apertures are excluded from the test material when determining moisture vapour permeability).

When used herein the term "air permeable" suitably means having an oxygen permeability of at least 500, more suitably at least 800, favourably at least 2,000 and preferably at least 5,000 ml/m$^2$/atmosphere. (A convenient method for determining gas permeability is that of British Standard 2782, method 514A, procedure 2).

The adhesive is most suitably a polyacrylate, polymethacrylate or polyvinyl ethyl ether adhesive (i.e. a polycrylate or polyvinyl ethyl adhesive) and is preferably a polyvinyl ethyl ether adhesive. A favoured polyvinyl ether adhesive for use is a mixture of high and low viscosity such as Bakalite EHBM and Bakalite EHBC or their equivalents (such as described in U.S. Pat. No. 364,535).

The wound closure is not necessarily moisture vapour permeable (for example it may have a moisture vapour permeability as low as 20 g/m$^2$/day but it has now been found that considerable unexpected advantages accrue if the skin closure of this invention has a good level of moisture vapour permeability. A effectively non-moisture vapour permeable film forming material which may be employed is a polyethylene. Apt moisture vapour permeable film materials which may be employed include polyurethanes. The film forming material used is normally a thermoplastic material. Thus favoured polyurethanes for use are thermoplastic polyurethanes such as Estane 5714F or its equivalent.

The biocompatible film used will generally be 20 to 70 microns thick for example 25 to 40 microns thick. Use of adhesives at a thickness of 10 to 60 microns is acceptable with a thickness of 20 to 50 microns being particularly apt. The total thickness of the polyurethane and adhesive layers is favourably from 40 to 120 microns and preferably from 50 to 70 microns.

In the past flexible adhesive skin closures of the type which has a central portion provided with apertures sufficient for the manipulation of wound edges have been in the form of a relatively narrow strip because the materials from which they were made were not suitable for use over large areas around wounds. The use of flexible, elastic, air permeable, films of polyurethane (or other material especially when moisture vapour permeable) coated on one side with an adhesive as described herein allows for the use of a broad wound closure of the preceding type which is not less than 6 cm wide as measured from edge to edge along the row of orifices at the wound covering area. A convenient shape for the closure will be a rectangle in which the ratio of the lengths of pairs of opposing edges is not greater than 1:2 and more suitably 2:3. Most aptly the closure will be square (that is opposing edges will be of equal length as this gives a particularly effective area of adhesion and correct tension across the wound. At present we envisage a maximum edge length as 30 cm and more usually not more than 20 cm with a minimum edge length of not less than 6 cms., more usually not less than 8 cm and preferably not less than 10 cm (the sizes referred to in the section refer to the adhesive covered zones and do not include any none adhesive handle ares or the like in which the adhesive is covered by a film). Closures with application areas of from 4 cm to 12 cm in width or 4 cm to 15 cm in length are suitable for many incisions.

In another aspect the invention provides a closure for application across a surgical incision or accidental lacerations to unite the edges thereof and hold them together during the healing process, consisting of a flexible sheet of air permeable and moisture vapour permeable synthetic polymeric material coated for adhesiion to skin with a pharmacologically acceptable pressure sensitive adhesive and divided into two portions for application under tension on to each side of the incision or laceration, with a notional straight line passing through the midpoints of a plurality of parallel elongate orifices; characterised in that the sheet is thin elastic material impervious to bacteria and liquid and is coated with the adhesive material over its whole application face; further characterised in that (a) the orifices are wide enough to permit any necessary manipulation of the edges of the incision or laceration before it heals, together with exudation of any liquid, but narrow enough to ensure firm union of the sides of the incision or laceration all along the dressing (b) the orifices are long enough to permit of each placement e.g. to accommodate a non-straight incision or laceration so that the wound falls beneath the orifies, all along its length, but short enough to permit the interposition material to maintain a resisting effect against lateral or perpendicular wound edge displacement, and (c) the spacing between the orifices or between a closure edge and its nearest orifice is large enough to exert a significant restraining action up to the edge of the incision or laceration and to ensure that the tensioned material does not press into the marginal tissue in the vicinity of the incision or laceration but small enough that it does not cover an area such as to trap liquid exudate.

There are a number of differences between the present invention and the prior art. Thus for example, in the present invention the adhesive layer, under the constraints and desiderata defined hereinbefore, extends as integral subareas over the united incisions or laceration edges, these subareas being separated by the orifices to the extent and for the reasons described. In the prior art the adhesive areas basically formed "anchor" zones attached to the skin, spaced from the wound and constituting the base for thread-like metal or otherwise effectively non-adherent tensioning members crossing the wound but not otherwise causing the wound edges to adhere.

The sheet or film of synthetic polymeric material can in theory be any coherent elastic sheet with the properties of permeability to air and moisture vapour, but not to liquid or bacteria. In practice, we have found thin sheets of less than 100 or even 50 microns to be preferable. Such thin sheets allow easy detection of good apposition of wound edges by touch. An especially advantageous material has been found to be that available under the trade mark "Op-Site" which is inter alia a surgical drape material, consisting of two thin continuous layers, one of elastic, flexible polyurethane and one of applied adhesive, in total about 50–55 microns thick. Such material has a moisture vapour permeability not normally less than 700 gm/m$^2$/day/at 100%–20% humidity and also stretches in two directions, giving therefore the possibility of good wound control both laterally and at right angles to the edges.

A typical adhesive especially for use in "Op-Site" comprises usually a blend of polyvinylethers, usually of a high viscosity grade and a low viscosity grade polyvinylether, but any other pharmacologically acceptable high adhesion synthetic low allergy pressure-sensitive adhesive (such as acrylates) of which there are numerous examples in the medical dressing art can be used if suitably moisture vapour permeable, and of good shear resistance.

The orifices in the closures preferably have rounded ends to prevent any tears being propagated when the closure is stretched into place. They allow passage of wound exudate (optionally to an overlying absorbent pad if used) but they should also be wide enough to permit inspection at spaced intervals along the wound to monitor healing (or in the early stages at least) to allow manipulation of the wound edge, for example by an occasional clip or stitch. If they are too wide, however, the edges of the wound may gap or displace in the middle of the orifice, with consequent scarring. Generally speaking, the orifices will therefore be from 2 to 10 mm wide, more preferably from 2 to 5 mm wide and usually about 3 mm wide.

The overall length of the orifices is conveniently such as to accommodate the fact that not all incisions or lacerations are exactly straight. Obviously, a markedly angled cut is best dealt with by more than one dressing, to preserve good restraint at the wound edges, but a slight curve or angle can be accommodated by a single closure. Also the orifice should be long enough to facilitate elongation of the intermediate faces, so as to pull the wound edges together. Aptly the orifices which are preferably elongate (that is longer than they are wide) are at least 5 mm long. If the orifices are too long the remaining material has too much lateral freedom and thus loses some of its desirable retaining power; the maximum length that is desirable for such orifices is aptly about 20 mm. Aptly the orifices are from 6 to 15 mm long and preferably about 10 to 12 mm long. The rounded end will of course add slightly to these dimensions, for example by an amount equivalent to the width if the ends are semi-circular.

The spacing of the orifices (from each other or from the edge of the dressing) plays an important part in the closure of this invention. Firstly, sheets of water-impervious materials such as "Op-Site" placed over wounds accumulate a reservoir of wound exudate. For some purposes such as burns therapy this may be desirable but often it is undesirable. Depending on such factors as the nature and volume of exudate, the wound and the tissue, there is a chance of such accumulation in a closure if more than 10 mm distance of adherent material has to be traversed before reaching an orifice. Thus the spacing of orifices is normally closer than 20 mm. This spacing prevents undue reduction in the number of wound inspection sites. However, if the spacing is too small there is insufficient adhesive to grip on the wound edges to prevent lateral or other displacement and (especially where there is a significant degree of stretch application), there may be excessive stretch and "necking" of the material which can then be cut into the soft new tissue and become embedded or cause ulcers. Usually, therefore, minimum spacing is about 6 mm, and preferably spacing is from 8 to 12 mm, for example about 10 mm.

The whole closure can be embodied in a convenient size for use in most locations of the body, and with easy manipulation. A closure with an application area of from 40 to 120 mm in width and 40 to 150 mm in length is generally convenient for handling and emplacement, and for the size of the incision and lacerations for which this invention is envisaged.

Although according to the invention the whole application face carries adhesive a medical technician will realise that non-adhesive gripping margins, well spaced from the orifices, can usefully be provided, the "application face" being the area between, but not including these margins.

While the closure itself i.e. the orificed adhesive sheet is a major aspect of the invention it will for convenience in storage and handling generally be mounted on a releasable throwaway backing sheet. This can be coextensive with the closure, and if desired similarly perforated, although it could be a simple paper or like roll supporting a supply of closures; in either case an intermediate release coating is advantageous. Such combinations all constitute aspects of the invention.

The invention will be further described with reference to the accompanying drawings which are broken away views of a closure mounted on a coextensible peelable backing.

In Drawing 1 a rectangular sheet of paper 1, 90×145 mm, is provided with a silicone-based release layer over its whole front face. To it is peelably adhered a sheet 2 of elastic polymeric material by virtue of a pressure-sensitive adhesive with coloured adhesive-free margins 3 defining between themselves an "application face" 110 mm long.

Along the midline M are spaced six identical elongate orifices each nominally 3 mm wide and 11 mm long (to the extremities of their rounded ends). The spacing between adjacent orifices or between each dressing edge and the nearest orifice is 10 mm.

The constitution of the sheet was a 27 micron film completely covered on one surface with a 27 micron thickness of adhesive. The film was composed of polyurethane, such that a load of 300 to 400 gm extended a 2.5 cm wide strip by 40% of its unstretched length. The adhesive was a 1:1 blend of high viscosity, and a low-viscosity polyvinylether, to give a composite material which was air-permeable and moisture vapour permeable, but impermeable to water and bacteria.

In use the closure was applied under tension (such that the orifices were stretched to nearly 20 mm) over an incision with its edges held together, and allowed to grip, giving rapid healing and no overall scarring or puckering of the wound.

The orifices may be made in the closure by any convenient means such as punching out from the otherwise finished sheet or crush cut from a strip which is then cut into the desired lengths.

As previously indicated the closures of this invention normally and preferably have a protective layer which covers the adhesive prior to use. Normally this protective layer is a silicone based release material.

The adhesive layer may be sterilised (for example with ethylene oxide) and maintenance of sterility aided by use of the protective layer which thus serves an additional purpose.

Drawing 2 shows a particularly favoured closure according to this invention. A rectangular sheet of paper 11, 100 mm×140 mm, is provided with a silicone-based release layer on its whole operative surface. To this is preferably adhered a sheet 12 of flexible elastic polyurethane by virtue of polyvinylether adhesive (Op-Site). The coloured non-adhesive margins (handles) 13 are each 2 cm wide so that between them is defined an "application face" 10 cm long. This "application face" is also 10 cm wide so that it is square. This embodiment is provided with six elongate orifices as in the embodiment described in the first drawing.

The embodiment in Drawing 2 has been found to be very effective in a private trial in which it was found to produce no localised tension or ischaemia at the wound edge, to greatly reduce foreign body reactions and risk of infection at the puncture site, to be strong and conform readily to the body contours, to allow correct appositioning of the wound via the orifices, to be sufficiently comfortable to be left in place for up to 14 days and to enhance the final cosmetic effect.

The embodiments in the drawings, like other embodiments of this invention, may be applied by removing the backing paper so as to expose the adhesive, applying the film to one side of the wound edge along the length of the incision, completely removing the backing paper and then applying the other half of the film to the other wound edge. Alternatively the backing paper may be completely removed prior to application and the area of the film containing the orifices is applied directly to the incision and the rest of the film is applied to the surrounding areas of the skin. The apposition of the wound edges may be achieved by means of forceps operating through the holes in the adhesive film. The film is normally applied under tension whereby the skin edges are held firmly together.

The embodiments in the drawings will normally be used alone but they may be used in conjunction with classical sutures when there is an incision under high tension.

What we claim is:

1. A flexible adhesive skin closure having a central portion provided with apertures sufficient for the manipulation of would edges wherein said skin closure is of rectangular shape in which the length of one pair of opposing edges is not more than twice that of the other pair of opposing edges and which in use consists essentially of a polyurethane film coated on one surface with an adhesive and which coated film is flexible, elastic, air permeable, impervious to bacteria and liquid and has a moisture vapor permeability of at least 500 g/m$^2$/day/40° C./100–20% relative humidity difference.

2. A skin closure according to claim 1 wherein the adhesive is a polyacrylate or polyvinylether adhesive.

3. A skin closure according to claim 1 wherein the film is a thermoplastic polyurethane.

4. A skin closure according to claim 1 wherein the elasticity of the film is such that a load of 300–400 g extends a 2.5 cm wide strip by 40% of its unstretched length.

5. A skin closure according to claim 1 in which the adhesive layer is in sterile form.

* * * * *